(12) United States Patent
Pham et al.

(10) Patent No.: US 8,168,804 B2
(45) Date of Patent: May 1, 2012

(54) LARGE STOKE SHIFT NIR DYES

(75) Inventors: Wellington Pham, Brentwood, TN (US); John C Gore, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 359 days.

(21) Appl. No.: 12/165,369

(22) Filed: Jun. 30, 2008

(65) Prior Publication Data
US 2009/0029405 A1    Jan. 29, 2009

Related U.S. Application Data

(60) Provisional application No. 60/947,293, filed on Jun. 29, 2007.

(51) Int. Cl.
*C07D 403/06* (2006.01)
*A61K 31/404* (2006.01)

(52) U.S. Cl. ........................................ 548/455; 514/414

(58) Field of Classification Search .................. 548/455; 514/414
See application file for complete search history.

(56) References Cited

U.S. PATENT DOCUMENTS

| | | | |
|---|---|---|---|
| 5,627,027 | A | 5/1997 | Waggoner |
| 6,403,807 | B1 | 6/2002 | Singh et al. |
| 6,593,148 | B1 | 7/2003 | Narayanan |
| 7,008,798 | B2 | 3/2006 | Waggoner |
| 7,230,117 | B2 | 6/2007 | Michael et al. |
| 2006/0239922 | A1 | 10/2006 | Cooper |

FOREIGN PATENT DOCUMENTS

JP    06145539 A * 5/1994

OTHER PUBLICATIONS

Pham et al. Chem. Commun., 2008, 1895-1897 (published on Feb. 28, 2008).*
Registry Entry for CAS registry No. 751456-10-7, (entered STN on Sep. 24, 2004).*
Registry Entry for CAS Registry No. 607709-65-9, which entered STN on Oct. 22, 2003.*
Machine translation of JP 06145539 A, translated Feb. 17, 2011.*
Achilefu, S.; Dorshow, R. B.; Bugaj, J. E.; Rajagopalan, R. Invest Radial 2000, 35, (8), 479-85.
Becker, A.; Hessenius, C.; Bhargava, S.; Grotzinger, C.; Licha, K.; Schneider-Mergener, J.; Wiedenmann, B.; Semmler, W. Ann N Y Acad Sci 2000, 921, 275-8.

(Continued)

*Primary Examiner* — Joseph Kosack
*Assistant Examiner* — Matthew Coughlin
(74) *Attorney, Agent, or Firm* — Stites & Harbison PLLC; Nicolo Davidson; Richard S. Myers, Jr.

(57) ABSTRACT

A compound of the following formula:

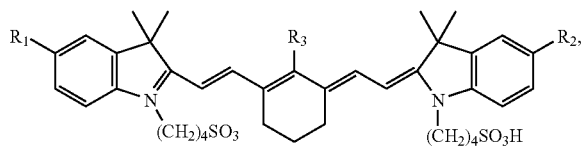

wherein $R_1$ is $SO_3H$; $R_2$ is chosen from carboxylic acid group and $SO_3H$; and $R_3$ is chosen from Cl, carboxylic acid group, amino, amino-carboxylic acid group, amido group, amino-amido group, and methods of use related to imaging.

8 Claims, 2 Drawing Sheets

Optical property of NIR dyes.

OTHER PUBLICATIONS

Bremer, C.; Tung, C. H.; Weissleder, R. Nat Med 2001, 7, (6), 743-8.
Fabian, J.; Nakazumi, H. Matsuoka, M.. Chemical Reviews (Washington, DC, United States) 1992, 92, (6), 1197-1226.
Hilderbrand, S.; Kelly, K.; Weissleder, R.; Tung, C.; Monofunctional near-infrared fluorochromes for imaging application; Bioconjugate Chem.; 2005; 16; 1275-1281.
Kiyose, K.; Kojima, H.; Urano, Y.; Nagano, T.; Development of a ratiometric fluorescent zinc ion probe in near-infrared region, based on tricarbocyanine chromophore; J. Am. Chem. Soc; 2006; 128; 6548-6549.
Lee, H.; Mason, Ch.; Achilefu, S.; Heptamethine cyanine dyes with a robust c-c bond at the central position of the chromophore; J. Org. Chem; 2006, 71, 7862-7865.
Licha, K.; Hessenius, C.; Becker, A.; Henklein, P.; Bauer, M.; Wisniewski, S.; Wiedenmann, B.; Semmler, W. Bioconjug Chem 2001, 12, (1), 44-50.
Marten, K.; Bremer, C., Khazaie, K.; Sameni, M.; Sloane, B.; Tung, C. H.; Weissleder, R. Gastroenterology 2002, 122, (2), 406-14.
Medarova, Z.; Pham, W.; Farrar, C.; Petkova, V.; Moore, A. Nat Med 2007, 13, (3), 372-377.
Medarova, Z.; Pham, W.; Kim, Y.; Dai, G.; Moore, A. Int J Cancer 2006, 118, (11), 2796-802.
Peng, X.; Song, F.; Lu, E.; Wang, Y.; Zhou, W.; Fan, J.; Geo, Y.; Heptamethine cyanine dyes with a large stokes shift and strong fluorescence; A paradigm for excited-state intramolecular charge transfer; J Am Chem Soc 2005, 127, (12), 4170-1.
Pham, W.; Choi, Y.; Weissleder, R.; Tung, C. H.; Developing a peptide-based near-infrared molecular probe for protease sensing; Bioconjug Chem 2004, 15, (6), 1403-7.
Pham, W.; Lai, W.; Weissleder, R.; Tung, Ch; High efficiency synthesis of a bioconjugatable near-infrared fluorochrome; Bioconjugate Chem.; 2003, 14, 1048-1051.
Pham, W.: Medarova, Z.; Moore, A.; Synthesis and application of a water-soluble near-infrared dye for cancer detection using optical imaging; Bioconjug Chem 2005, 16, (3), 735-40.
Pham, W.; Zhao, B. Q.; Lo, E. H.; Medarova, Z.; Rosen, B.; Moore, A. Neuroimage 2005, 28, (1), 287-92.
Pham, W; Cassell, L.; Gillman, A.; Koktysh, D.; Gore, John C.; A near-infrared dye for multichannel imaging; Chem. Commun.; 2008, 1895-1897.
Tung, C.-H.; Bredow, S.; Mahmood, U.; Weissleder, R.; Preparation of a cathepsin d sensitive near-infrared fluorescence probe for imaging; Bioconjugate Chem 1999, 10, (5), 892-896.
Tung, C. H.; Mahmood, U.; Bredow, S.; Weissleder, R.; In Vivo Imaging of Proteolytic Enzyme Activity Using a Novel Molecular Reporter; Cancer Res 2000, 60, (17), 4953-8.
Weissleder, R.; Tung, C. H.; Mahmood, U.; Bogdanov, A., Jr. Nat Biotechnol 1999, 17 (4), 375-8.
Zaheer, A.; Lenkinski, R. E.; Mahmood, A.; Jones, A. G.; Cantley, L. C.; Frangioni, J. V. Nat Biotechnol 2001, 19, (12), 1148-54.

* cited by examiner

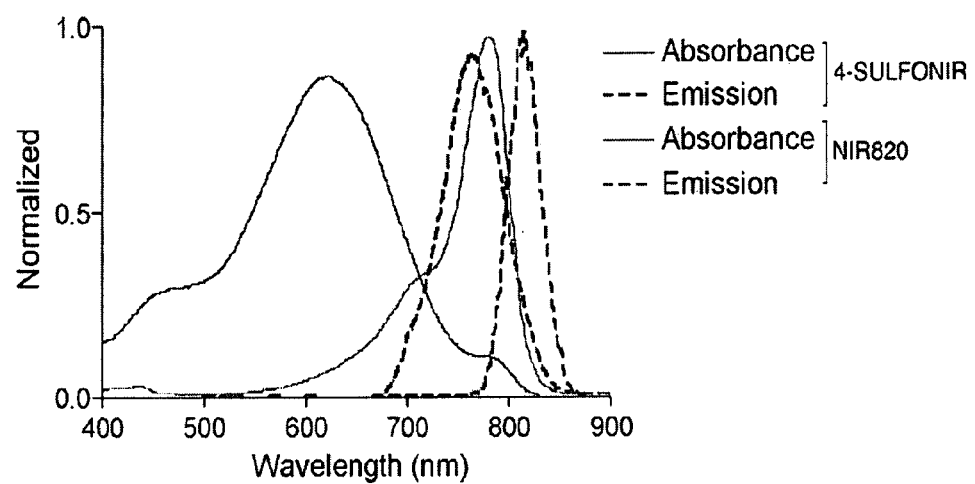
Figure 1. Optical property of NIR dyes.

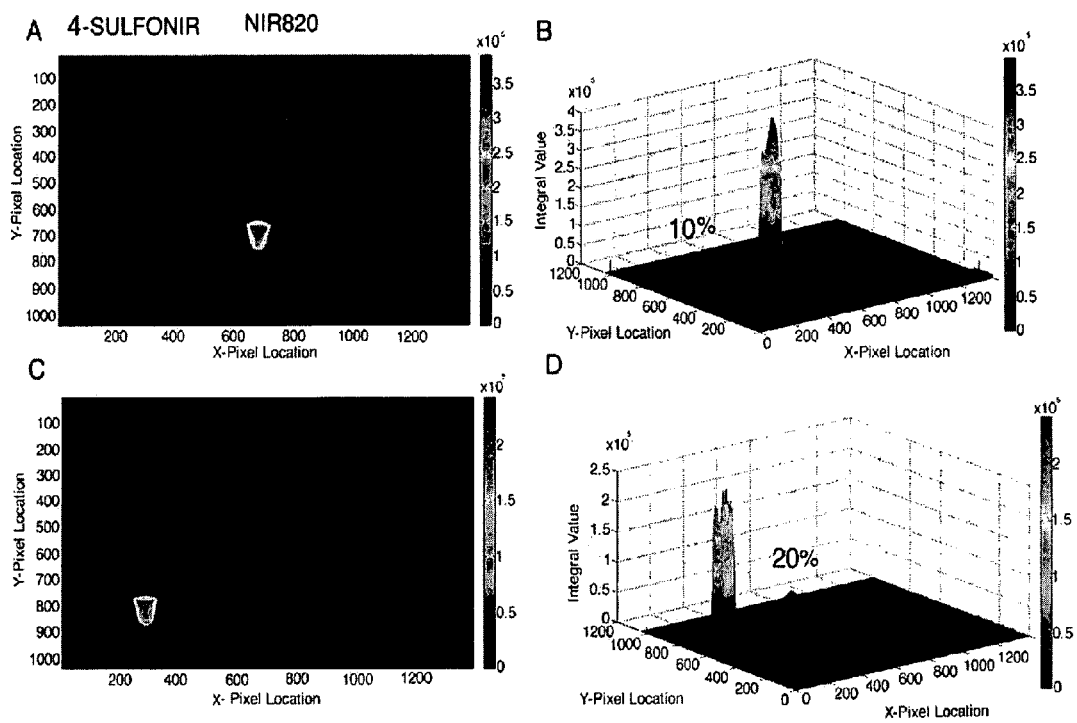
Figure 2. Quantitative analysis of fluorescent images of two dyes pertaining to detect two distinguish events in one environment.

LARGE STOKE SHIFT NIR DYES

PRIOR APPLICATION

This is a patent application claiming priority under 35 U.S.C. §119(e) of Provisional Patent Application No. 60/947,293 filed Jun. 29, 2007. The content of the application is incorporated herein by reference in their entirety.

GOVERNMENT SUPPORT

This invention was made with support from Grant Number KAG026366A from the National Institute on Aging. The United States government has certain rights to this invention.

FIELD OF THE INVENTION

The present invention relates, generally, to the field of optical molecular imaging.

BACKGROUND OF THE INVENTION

Optical molecular imaging is an attractive modality that has been employed recently in many aspects of biomedical research aiming at using light to detect cellular and molecular events in vivo. This targeted imaging technique largely relies on near-infrared (NIR) dyes that emit light in the NIR window (700-900 nm). Imaging in this range is of importance because of the increased tissue penetration and reduced absorption by physiologically abundant molecules such as hemoglobin (600 nm) and water (>1200 nm) compared to other wavelengths. Optical dyes operate by absorbing energy at one wavelength but the reemitting light at a longer wavelength. The difference in the absorbed and emitted wavelengths (the Stokes shift) is an important feature of the dye because it affects how well the dye can be detected reliably. Most current NIR dyes have rather poor performance because of their Stokes shift is small (30 nm).

Without being bound by theory, part of the explanation is the rigid structure of the current dyes that have unsaturated polymethine backbones. This affects on the ability to separate the excitation from the emission photons discretely, thus limiting the ability to image multiple wavelengths and causes tremendous cost in the effort to create steep-edge bandpass filters in detection to cope with this problem. The present inventors have used a novel approach to generate large Stokes shift NIR dyes using a conventional intramolecular charge transfer mechanism.

Most near-infrared dyes currently available in the market have very narrow Stokes shift (~30 nm). This may result in cross-talk during imaging processing. On the other hand, embodiments of the present invention have larger Stokes shift (at least about 100 nm, and in embodiments of the invention, about 150 nm); in addition, the excitation spectrum is very wide, which allows excitation of the dye in the visible range while collecting the emission photons in the near-infrared window. This feature allow researchers to image multiple wavelengths corresponding to several molecular events in one target using these dyes.

BRIEF DESCRIPTION OF THE INVENTION

Embodiments of the present invention relate to compounds useful for the labeling of biological materials, such as DNA and proteins, and non-biological materials to make the materials fluorescent and easily detectable.

One embodiment of the present invention is a compound of the following formula:

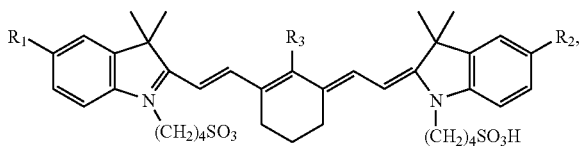

wherein $R_1$ is $SO_3H$; $R_2$ is chosen from carboxylic acid group and $SO_3H$; and $R_3$ is chosen from Cl, carboxylic acid group, amino, amino-carboxylic acid group, amido group, amino-amido group.

In another embodiment of the present invention, $R_1$ and $R_2$ are $SO_3H$.

In another embodiment, $R_3$ is amino-carboxylic acid group.

In another embodiment, $R_3$ is —N—$(CH_2)_{1-20}$COOH.

In another embodiment, $R_3$ is:

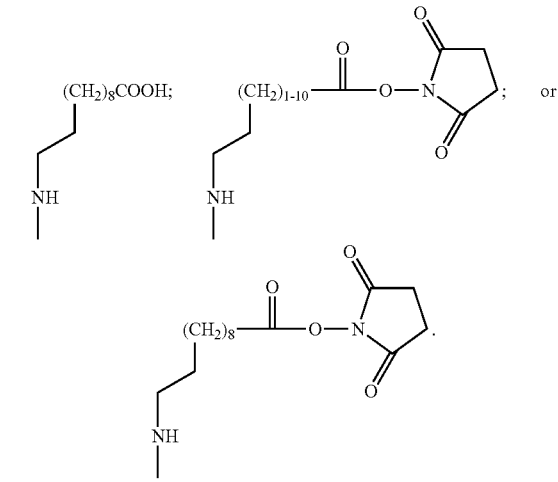

In another embodiment, $R_3$ is chosen from:

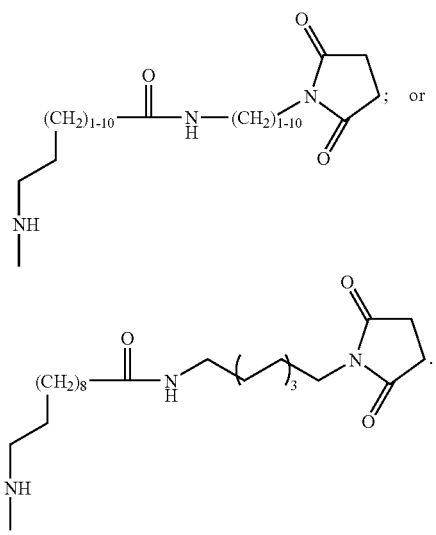

Accordingly, a compound of the present invention is of the following formula:

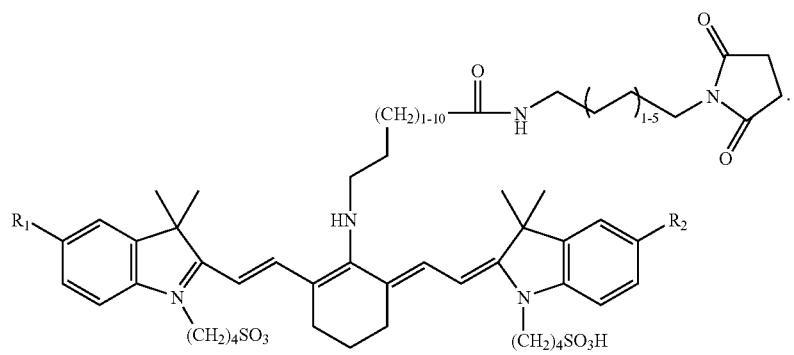

Another compound of the present invention is of the following formula:

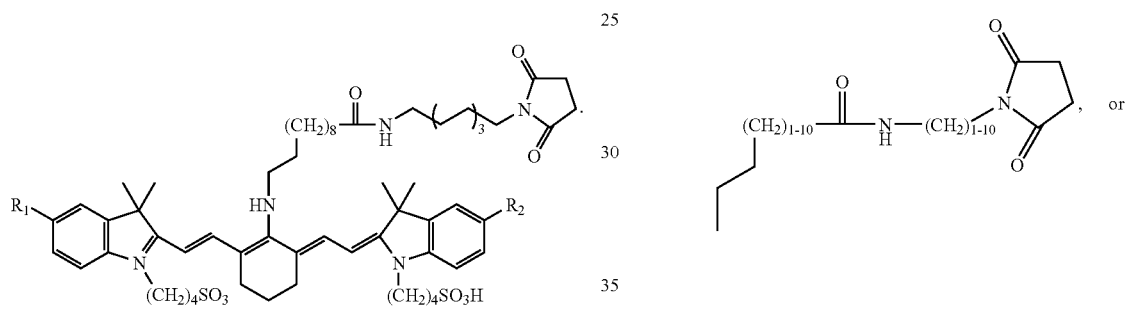

Another compound of the present invention is of the following formula:

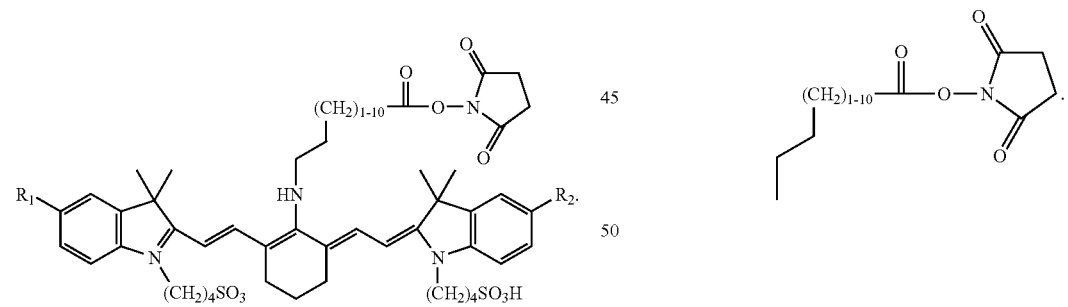

Yet another compound of the present invention is of the following formula:

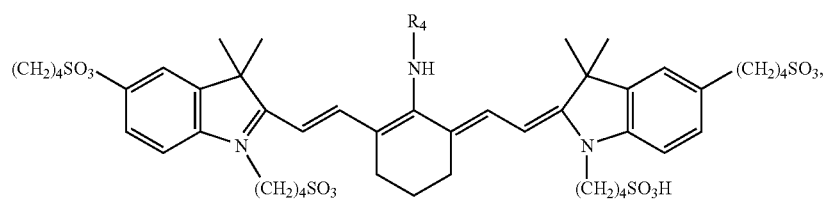

wherein $R_4$ is chosen from a carboxylic acid group, amido group, amino-amido group.

$R_4$ may also be chosen from:

Another embodiment of the present invention is a conjugate comprising a biological molecule and a compound chosen from:

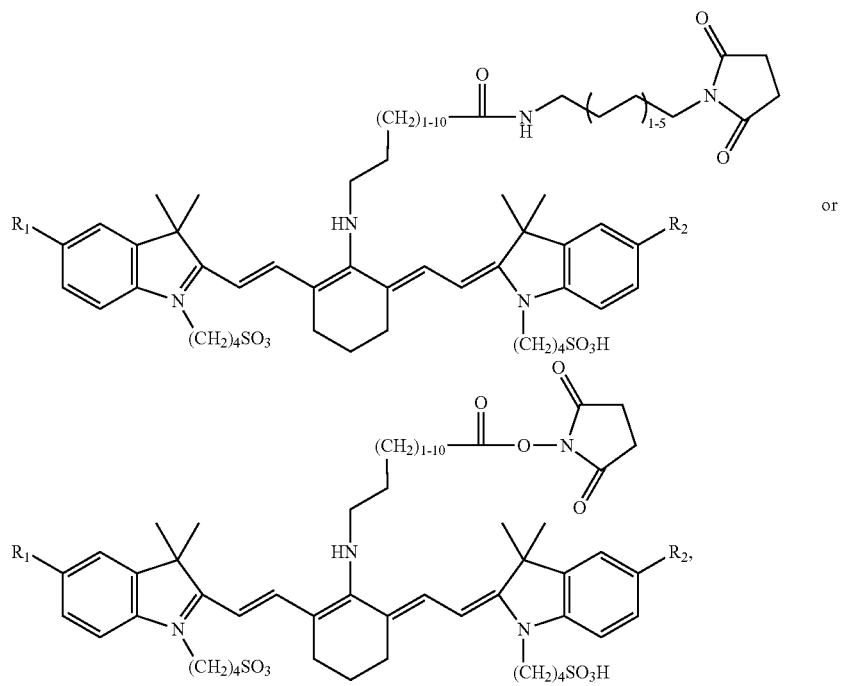

or a conjugable form thereof.

Examples of the biological components include antibodies, proteins, peptides, enzyme substrates, hormones, lymphokines, metabolites, receptors, antigens, haptens, lectins, toxins, carbohydrates, sugars, oligosaccharides, polysaccharides, nucleotides, derivatised nucleotides, nucleic acids, deoxynucleic acids, derivatised nucleic acids, derivatised deoxynucleic acids, DNA fragments, RNA fragments, derivatised DNA fragments, derivatised RNA fragments and drugs.

Another embodiment of the present invention is a method of imaging a sample of cells, comprising:

providing a compound of the present invention, specifically including but not limited to the following:

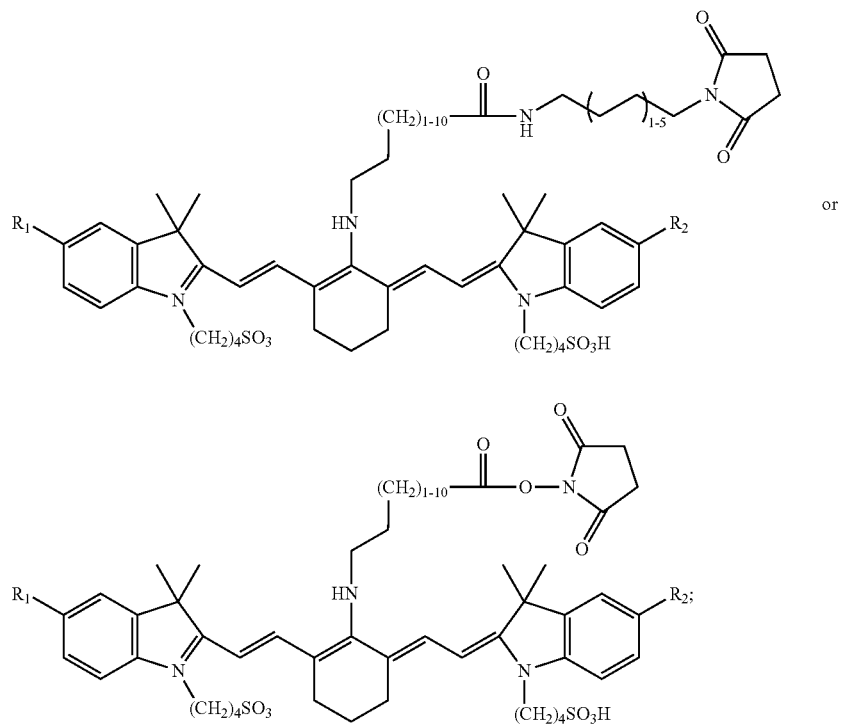

forming a conjugate with said compound and a biological molecule; introducing said conjugate to a sample of cells; exciting said conjugate; detecting said conjugate. The biological molecule may include those specifically described herein.

BRIEF DESCRIPTION OF THE FIGURES

FIG. 1 is a graph comparing optical properties of NIR dyes.

FIG. 2 shows quantitative analysis of fluoresecen images of two dyes pertaining to detect two distinguish events in one environment.

DESCRIPTION OF EMBODIMENTS OF THE INVENTION

The development of near-infrared (NIR) dyes is typically a rate-limiting step in any potential advancement and translation of in vivo optical molecular imaging. Since scattering and auto-fluorescence decrease with increasing wavelength, NIR fluorescent dyes offer a considerable advantage over blue-shift dyes. Specifically, because fluorescent labels associated with NIR emission wavelengths can penetrate tissue deeper than those associated with blue emission wavelengths, imaging in the NIR window provides enormous potential for non-invasive in vivo imaging applications.

Recently, several NIR fluorescence dyes based on cyanine scaffolding have demonstrated great promise for in vivo imaging of biological targets such as somatostatin receptors (see, for example, Achilefu, S. et al., Invest Radiol 2000, 35; (8), 479-85; Becker, A. et al., NY Acad Sci 2000, 921, 275-8; and Licha, K. et al., Bioconjug Chem 2001, 12, (1), 44-50; all of which are incorporated here by reference), osteolastic activity (see, for example, Zaheer, A. et al., Nat Biotechnol 2001, 19, (12), 1148-54; incorporated herein by reference) and proteases (see, for example, Bremer, C. et al., Nat Med 2001, 7, (6), 743-8; (see Marten, K. et al., Gastroenterology 2002, 122, (2), 406-14; Medarova, Z. et al., Nat Med 2007, 13, (3), 372-377; and Medarova, Z. et al, Int J Cancer 2006, 118, (11), 2796-802, all of which are incorporated herein by reference).

Most NIR dyes belong to the family of cyanine, rhodamine or oxazine organic molecules. Cyanine dyes are at times preferred to the others in this family because in addition to having high absorption coefficients, the NIR feature associated with the electron effect can be easily tuned by varying the length of the vinylene bridge between the hetero-cyclic indole rings. Furthermore, modifications can be made on the indole rings as well as on the polymethine chain to satisfy imaging requirements such as NIR range emission, water solubility, stability in a wide range of chemistries, and finally, the inclusion of a functional group for bioconjugation. It has been demonstrated that the length of the cyanine bridge, rather than the size of the aromatic ring system, determines the bathochromic shift of the dye. The stability of the dye decreases significantly when the number of unsaturated carbon bonds is equal to 7. However, the absorbance intensity of cyanine dyes increases as the chain length is extended.

To overcome the instability problem, the present inventors have developed cyclic polymethine dyes (see, for example, Formula 1, where $R_1$ and/or $R_2$ may also be a functional group for conjugation). The $NIR_{820}$ dye has a central methine incorporated into a ring system that minimizes the flipping. The resulting high stability of the dye enables its conjugation to protein, peptide in solution and solid phase chemistry in varying chemical conditions.

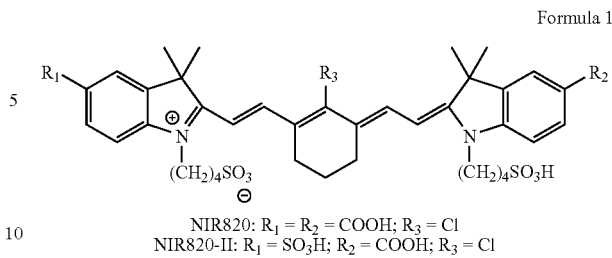

NIR820: $R_1 = R_2 = COOH$; $R_3 = Cl$
NIR820-II: $R_1 = SO_3H$; $R_2 = COOH$; $R_3 = Cl$

To improve water solubility for intravenous injection into mouse models, the present inventors modified the NIR820 dye to create dyes of the present invention, a second generation, NIR820-II, using an asymmetric approach in which one additional sulfonate group was derivatized on the indole ring. The enhancement of water solubility had the additional effect of improving the quantum yield, albeit with intensive purification effort and low reaction yield.

These compounds are useful for labeling biological and non-biological molecules.

Thus, embodiments of the present invention are useful as labels of biological and nonbiological molecules. Biological molecules include, but are not limited to, natural and synthetic DNA, RNA, PNA (peptide nucleic acids) peptides, proteins, cells, antibodies, antigens, haptens, polysaccharides, oligosaccharides, carbohydrates, avidin, streptavidin, hormones, enzyme substrates, nucleosides, nucleotides and analogs thereof. Preferred biological molecules are DNA and RNA, PNA, oligonucleotides, nucleosides and nucleotides or analogs thereof, such as dideoxynucleotides (terminators). Nonbiological molecules can include, for example, trace compounds, the presence of which in test samples is to be detected.

The compounds of this invention can be attached, for example, to analogs of nucleotide triphosphates (dNTPs and ddNTPs) to provide a reagent for enzymatic labeling of various DNA molecules and for facilitating their detection with an automated DNA sequencing and analysis system. See, Narayanan, N., et al., Near-Infrared Dyes for High Technology Applications, S. Daehne et al. (eds.) 1998, Kluwer Academic Publishers (1998), pp. 141-158, incorporated herein by reference. DNA sequencing reaction products can be labeled internally by performing limited polymerization utilizing the labeled dNTP as the sole source of a particular deoxynucleotide prior to a dideoxy-specific termination reaction. PCR products also can be labeled fluorescently by the addition of limited quantities of the labeled dNTP to the amplification reaction. Such labeling can be useful, for example, for the detection of short tandem repeat polymorphisms (STRPs), which in turn are useful for gene mapping, genetic diagnostics, forensic analyses and paternity testing.

Examples of nucleotide analogs and DNA chain terminators that can be labeled with the dyes of this invention include those listed, for example, in U.S. Pat. Nos. 5,332,666; 5,151,507; 5,047,519; 5,091,519; 4,711,955 and 5,241,060 and PCT Application publication WO 9504747.

The compounds of the present invention can be used according to U.S. Pat. No. 6,593,184, the contents of which are incorporated herein by reference.

Additionally, the compounds of the present invention can be used for the purpose of detection and quantification of labeled components as described in U.S. Pat. No. 7,008,798, incorporated herein by reference. That is, the dyes of the present invention can be used to label biological materials such as nucleic acids, proteins, carbohydrates, sugars, cells and combinations thereof as outlined in US '798. Thus, the dyes of the invention can label antibodies, antigens, avidin, peptides, derivatized nucleotides, bacteria, viruses, blood cells, tissue cells, hormones, lymphokines, trace biological molecules, toxins and drugs. Additionally, the dyes of the present invention can also be used to label non-biological materials, such as soluble polymers and polymeric particles, glass, monomers, drugs and other surfaces and particles which contain or are derivatized to contain functionalities capable of binding covalently to the amino, hydroxy or sulfhydryl reactive nucleophiles of the cyanine dye molecule.

An embodiment of the present invention is made as shown below. In this regard, below is the symmetric synthesis of the dye by condensation of disulfonated indole 1 with the knoevenegal iminium abduct 2 in the presence of sodium acetate and ethanol. The dye intermediate 3 contains 4 sulfonate groups, enabling isolation from other less water-soluble byproducts, such as the aniline from the elimination process or the product of semi-condensation (absorbs at $\lambda_{max}$=650 nm). A difference in polarity facilitates simple purification with decent yield. Nucleophilic substitution ($S_{NR1}$) at the central vinylogous halide carbon ($C(sp^2)$—X) by amine from aminoundecanoic acid 4 at an elevated temperature provides the final product, 4-SULFONIR. Embodiments of this product include the functional group of carboxylic acid as a site for activation, a required feature for in vivo application.

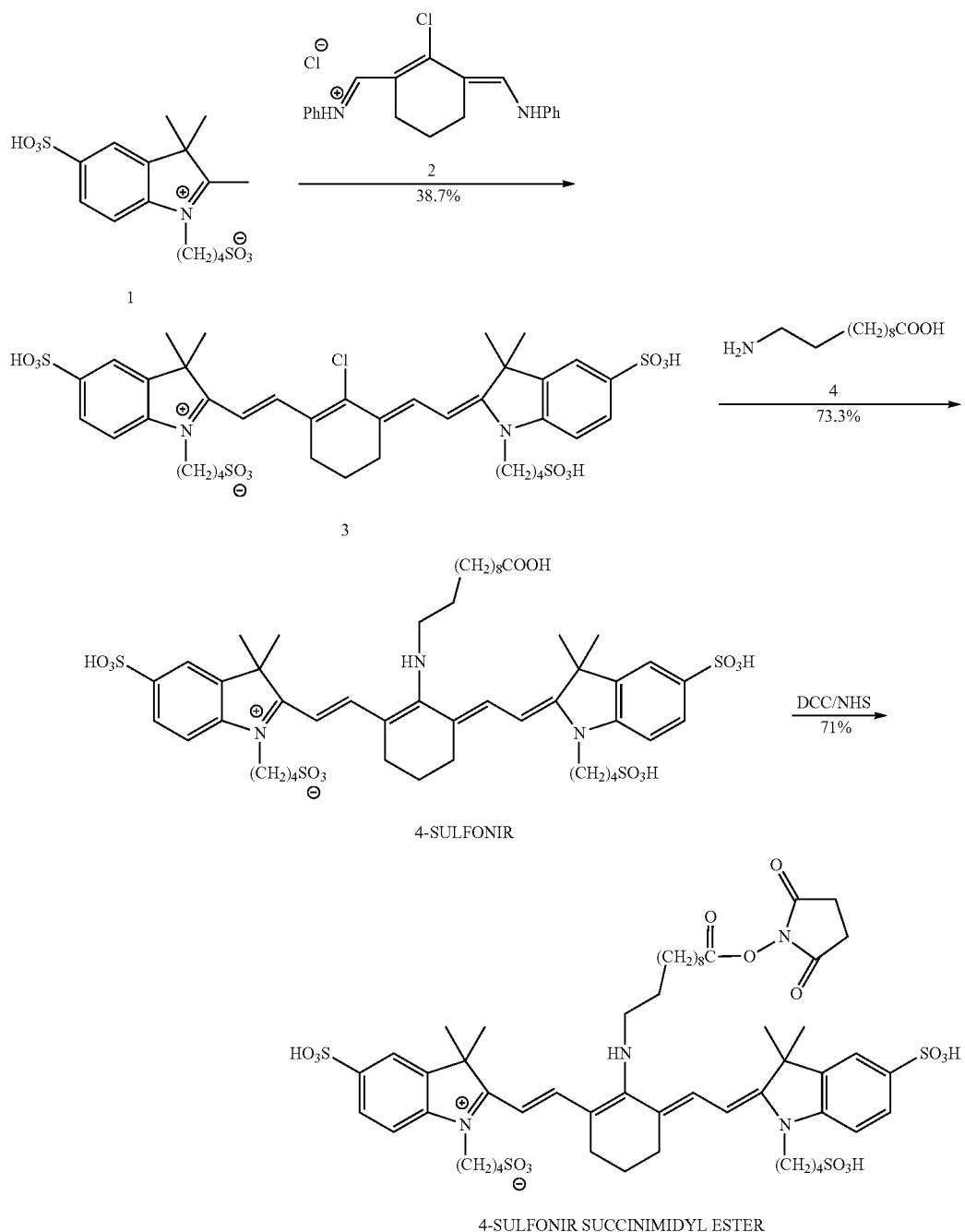

The alkylation process can be monitored by a change in the color of the dye. Specifically, the completion of the reaction is indicated by a color change from green to blue, corresponding to a shift in the absorbance from 790 nm to 600 nm. The relative quantum yield of 4-SULFONIR, compared to indocyanine green, is 0.37 in water while the molar extinction coefficient of 4-SULFONIR is $1.8 \times 10^5$ $M^{-1}cm^{-1}$ in the same medium. It is likely that an additional sulfonate group causes the enhanced water solubility, thus reducing hydrophobic-mediated quenching effects. In previous work, we have demonstrated that the quantum yield of NIR820-II is nearly double that of NIR820 because the latter is more water soluble.

Similarly to other cyanide dyes, the absorbance bands of 4-SULFONIR are created by the electronic transition contributed from the π electrons across the polymethine bridge; via substitution with a nitrogen molecule whose free pair of electrons contribute to the intramolecular charge transfer. During the course of work, we found that Peng et. al. also observed similar phenomena and have described this mechanism.

The Stoke's shift of this family of cyclic heptamethinylated cyanine dyes depends on the location of their functional group. If the indole ring system is functionalized, the Stoke's shift is ~30 nm (FIG. 1). However, the Stoke's shift expands to 140 nm when the functional group is on the methine bridge (FIG. 1). Using the carboxylic acid functional group, our experiments demonstrate the feasibility of activation of 4-SULFONIR as a succinimide ester intermediate for labeling applications. It should be noted, though, that the stability of 4-SULFONIR is one of several advantages of the present invention over other dyes, inasmuch as it supports convenience in work by eliminating the concern of decay caused by exposure to light or room temperatures.

In general, synthesis of a symmetric dye provides better yield than that of its asymmetric counterpart. The present inventors have observed that the condensation did not go to completion, as a significant amount of "semi-condensation" product was always present. This incompletion was also demonstrated in our previous work in which refluxing compound 1 and iminium 2 in absolute ethanol for several hours before the addition of other indole intermediate in an asymmetric synthesis. The outcome was consistently a nearly 1:1 ratio of the desired asymmetric and the undesired symmetric dye products. Without being bound by theory or mechanism, this observation explains why dye synthesis consistently results in low reaction yield and purification complications since the product and byproduct have very similar polarities.

Embodiments of the present invention include imaging two molecular events in one tissue. See the Examples and FIG. 2.

Additionally, embodiments of the present invention include the following compounds for labeling with amine reactive groups, including reactive groups that include peptides, proteins, antibodies, and other small biological/organic molecules. An example is a compound of the following formula:

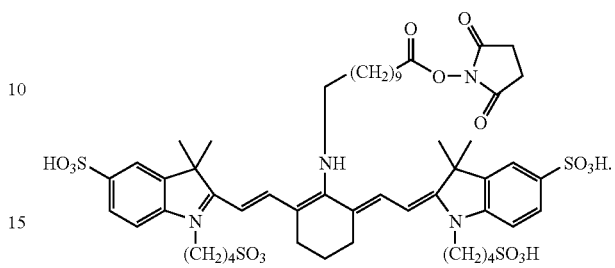

This compound can be made as follows:

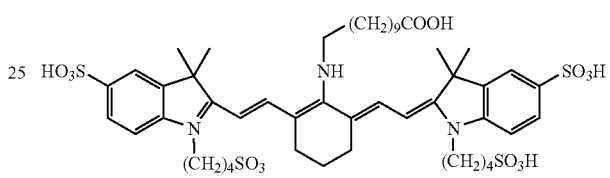

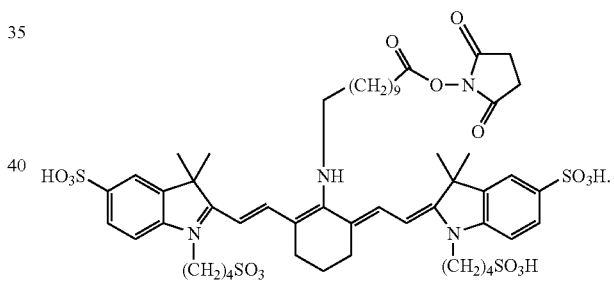

Additionally, embodiments of the present invention include the following compounds for labeling with thiol reactive groups, including reactive groups that include peptides, proteins, antibodies, and other small biological/organic molecules. An example is a compound of the following formula:

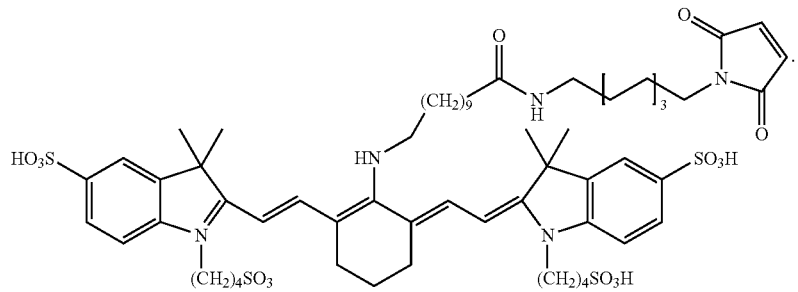

This compound can be made as follows:

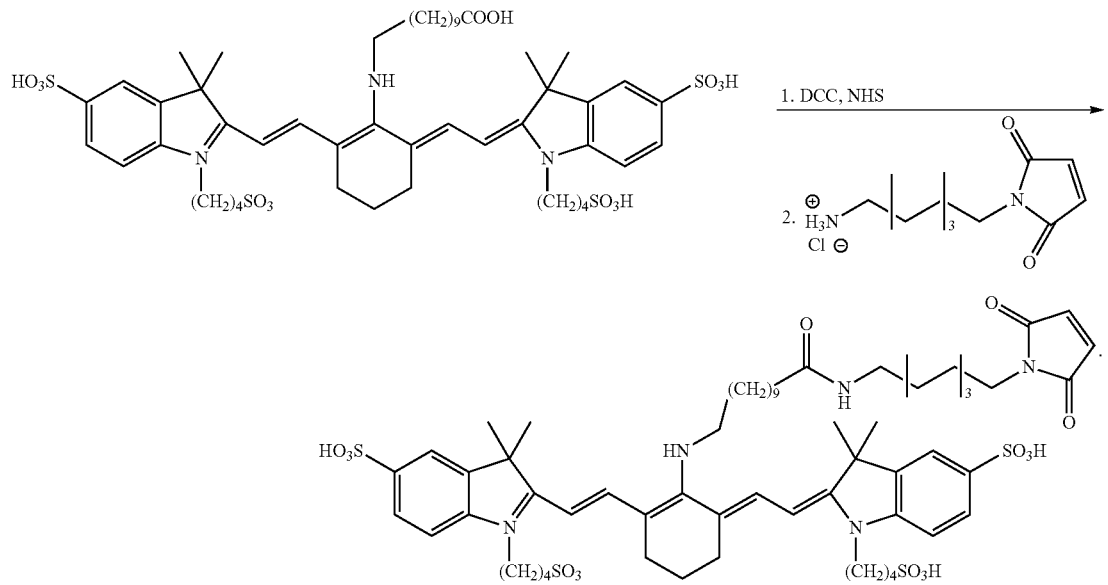

EXAMPLES

The following examples are presented to be exemplary of the present invention and methods of making and using thereof, and is not to be construed as be limiting thereof.

Example 1

Synthesis of Dye Intermediate 2

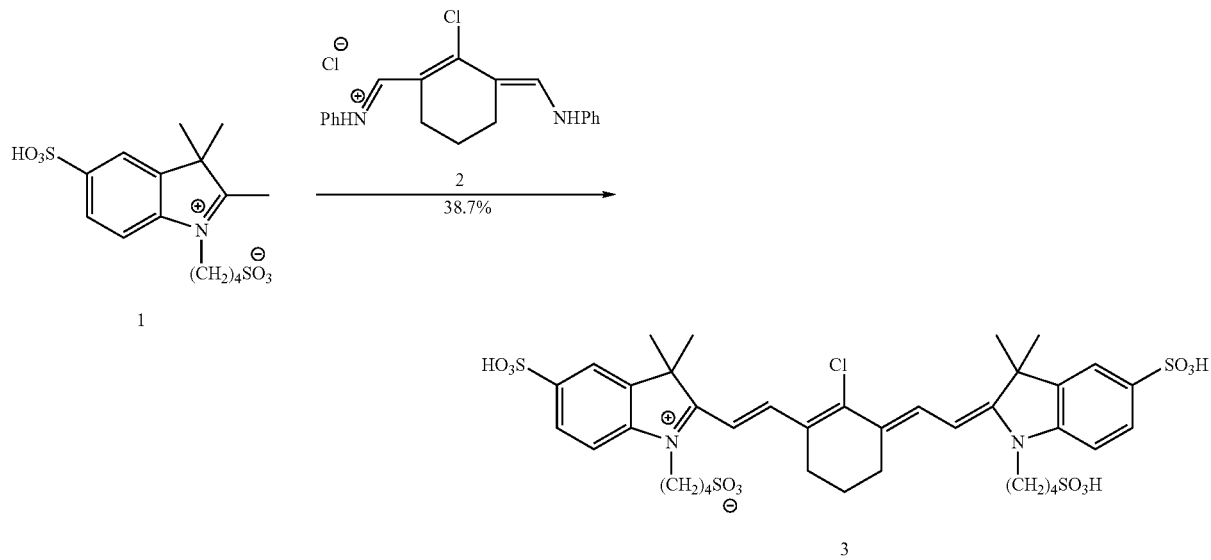

Sodium acetate (1.1 g, 0.013 mol) was added to a stirred suspension of disulfonated indole 1 (5 g, 0.013 mol), which was synthesized from our lab 1, and N-[(3-(anilinomethylene)-2-chloro-1-cyclohexen-1-yl)methylene]aniline 2 (2.3 g, 0.006 mol) in absolute ethanol at room temperature. The resulting red suspension was heated to reflux for 5 h. After cooling to room temperature, the solvent was decanted. The product was collected by filtering through a fine sinter glass filter and washed several times with methanol. The dark blue solid was dried. The yield of the crude product was 4.571 g (38.7%).

$^1$H NMR (400 MHz, D$_2$O); 8.30 (2H, d, J=14 Hz, vinyl CH), 7.87 (2H, s, Aryl CH), 7.79 (2H, d, J=8.4 Hz, Aryl CH), 7.32 (2H, d, J=8.4 Hz, Aryl CH), 6.21 (2H, d, J=13.6 Hz, vinyl CH), 4.129 (4H, t, br, CH$_2$—SO$_3$H), 2.95 (4H, t, J=6.6 Hz, N—CH$_2$, 2.54 (4H, t, br, cyclohexene CH$_2$), 1.86 (10H, m, SO$_3$=CH$_2$—CH$_2$—CH$_2$+cyclohexene CH$_2$), 1.70 (12H, s, —C—(CH$_3$)$_2$. MS (EI): calcd M$^+$ (C$_{38}$H$_{48}$ClN$_2$O$_{12}$S$_4$) 885.50, found 885.12.

Example 2

Synthesis of 4-SULFONIR

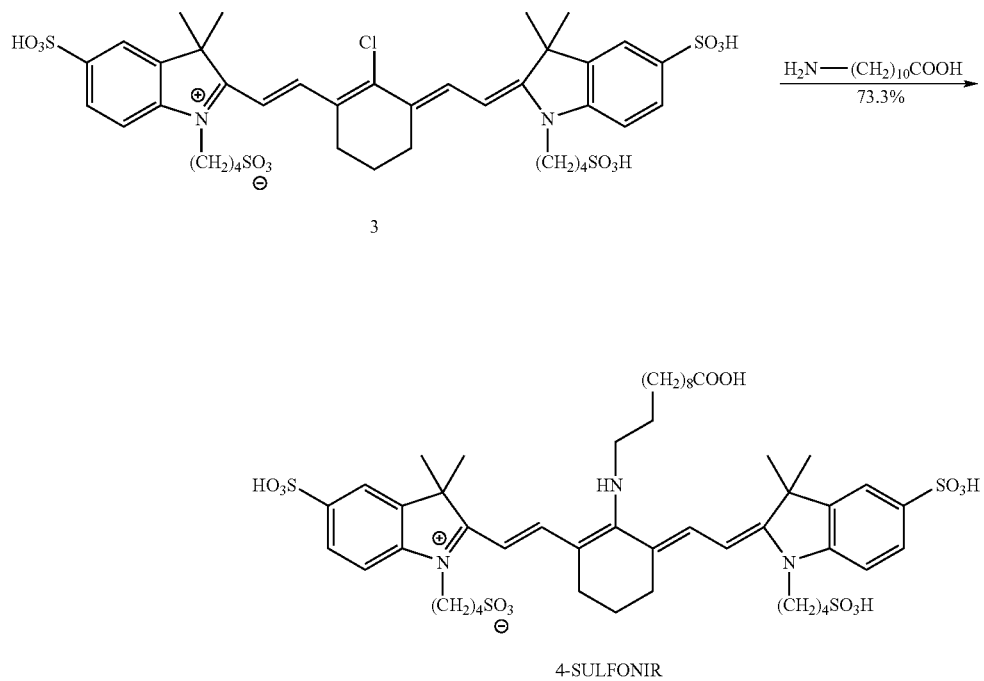

A suspension of Aminoundecanoic acid (137 mg, 0.68 mmol) and dye intermediate 3 (403 m, 0.45 mmol) in DMF was heated slightly at 80° C. for 3 h. During this time, the reaction mixture was green. When the reaction was completed, the color changed to blue. This indicated the presence of the alkylation product, which was precipitated in ether to afford a final yield of 73.3%.

$^1$H NMR (400 MHz, D$_2$O); 7.77 (2H, d, J=8.4 Hz, Aryl CH), 7.74 (2H, s, Aryl CH), 7.68 (2H, d, J=14.0 Hz, Vinyl CH), 7.10 (2H, d, J=8.2 Hz, Aryl CH), 5.85 (2H, d, J=14 Hz, Vinyl CH), 3.9 (4H, t,t br, CH$_2$—SO$_3$H), 3.22 (1H, t, J=7.8 Hz, NH), 3.0 (4H, t, J=8.0 Hz, N—CH$_2$, 2.52 (4H, t, J=6.6 Hz, cyclohexene CH$_2$), 2.18 (2H, q, J=8.0 Hz, NH—CH$_2$), 1.76-1.95 (10H, br, SO$_3$—CH$_2$CH$_2$ and cyclohexene CH$_2$), 1.65 (12H, s, —C—(CH$_3$)$_2$), 1.54 (4H, m, CH$_2$—COOH and NH—CH$_2$CH$_2$, 1.32 (14H, s, br, NH—CH$_2$—CH$_2$(CH$_2$)$_7$—CH$_2$—COOH).

MS (EI): calcd M$^+$ (C$_{49}$H$_{69}$N$_3$O$_{14}$S$_4$) 1052.34, found 1052.37.

Example 3

Synthesis of 4-SULONIR SUCCINIMIDYL ESTER

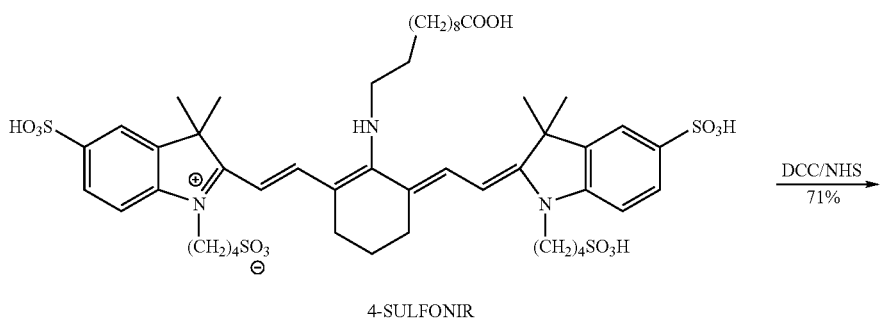

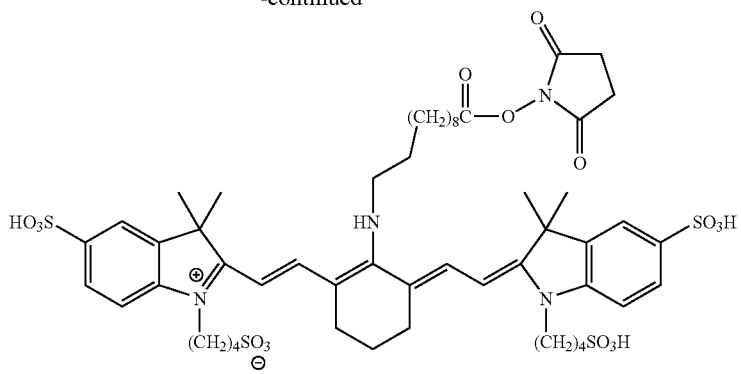

4-SULFONIR SUCCINIMIDYL ESTER

A stirred and homogenous solution of 4-SULFONIR (227 mg, 0.218 mmol) in DMF was added to Dicylohexylcarbodiimide (45 mg, 0.218 mmol) and N-hydroxysuccinimide (25.1 mg, 0.218 mmol). The resulting solution was left to stir at room temperature for 1d. This was then followed by purification via HPLC to afford 4-SULFONIR SUCCINIMIDYL ESTER with 71% yield.

$^1$H NMR (400 MHz, $D_2O$); 7.76 (4H, m, Aryl C$\underline{H}$), 7.71 (2H, d, J=13.5 Hz, Vinyl C$\underline{H}$), 7.11 (2H, d, J=8.4 $\overline{Hz}$, Aryl CH), 5.89 (2H, d, J=13 $\overline{Hz}$, Vinyl CH), 3.93 (4H, t,t, br, $\overline{CH_2}$—$SO_3H$), 3.53 (1H, t, J=7.5 Hz, $\overline{NH}$), 2.95 (4H, t, J=6.4 $\overline{Hz}$, N—$CH_2$), 2.83 (4H, s, —CO—$CH_2$—$CH_2$—CO), 2.41 (4H, br, cyclohexene $CH_2$, 1.68-1.83 $\overline{(12H, br}$, NH—$CH_2$, $SO_3$—$CH_2$—$CH_2$—$\overline{CH_2}$ and cyclohexene $CH_2$), 1.53 (12H, s, —C—$\overline{(CH_3)_2)}$, 1.2 $\overline{(18H}$, s, br, NH—$\overline{CH_2}$—$(CH_2)_{18}$CO).

MS (EI): calcd M$^+$ ($C_{53}H_{72}N_4O_{16}S_4$) 1147.42, found 1147.32.

Example 4

An Embodiment of the Present Invention Pertaining to Imaging Two Molecular Events in One Tissue The fluorescent signals of equal concentrations of 4-SULFONIR and NIR820 in two distinct phantom tubes are quantified. The latter dye has absorbance and emission at 790 nm and 820 nm, respectively. Both data sets were acquired using a Cambridge Research and Instrumentation, Inc., Maestro™ Optical Imaging System. The Maestro's "flat-field" correction function was used to compensate for possible illumination field inhomogeneities, and the data was single-binned to maximize resolution. When we excited the dyes in the NIR channel, NIR820 emitted a significantly stronger fluorescence signal than did 4-SULFONIR (FIG. 4A). In contrast, when the channel was switched to visible light, under the same settings (supporting information), the 4-SULFONIR lit up with remarkable intensity (FIG. 4C).

A quantitative analysis of the data was conducted using in-house developed Matlab programs. Our analysis revealed that, when excited in the NIR range (>750 nm), NIR820 emitted about 90% of the total fluorescence signal ($4.1 \times 10^8$ arbitrary intensity units), while 4-SULFONIR emission accounted for only about 10% ($3.4 \times 10^7$ arbitrary intensity units) of the total signal (FIG. 4B). To monitor an event linked to 4-SULFONIR, the same process was repeated with excitation in the visible range. In this domain, the 4-SULFONIR emitted approximately 80% of the total signal ($2.7 \times 10^8$ arbitrary intensity units) while the NIR820 emitted around 20% ($6.3 \times 10^7$ arbitrary intensity units) of the total signal (FIG. 4D). From these results, we determined that NIR820 and 4-SULFONIR can be used to image two events in one environment.

Thus, embodiments of the present invention are stable, water-soluble, and bioconjugatable NIR dyes with an improvement over traditional NIR dyes in quantum yield. The design of this dye features a time- and cost-efficient purification process. In addition, we demonstrate the proof-of-principle for using this large Stoke's shift dye for multichannel imaging with collection in the NIR spectrum. See FIG. 2.

Chemical shifts are reported in parts per million relative to a (or the) water peak at 4.80 ppm, and coupling constants are reported in hertz. Reverse phase HPLC purification was performed on a Hitachi Lachrome Elite incorporated with a Diode Array detector L-2455 using a Vydac 218TP1010 $C_{18}$ column (Hesperia, Calif.). The elution gradient was set from 0 to 50% of acetonitrile in protonated, deionized water. Detection was monitored in the 200-700 nm range. Absorption and emission spectra were determined using an Agilent UV-Vis instrument and a PTI QM-4SE fluorometer, respectively. Low resolution maldi-tof and high-resolution exact mass measurements (ESI) were determined from the Vanderbilt Mass Spectrometry Core Facility. All compounds were stored dried at −20° C. All assays were performed on freshly prepared samples.

Example 5

Quantification of a Fluorescence Signal of Each Dye in their Respective Ranges Dye samples were imaged twice using the Maestro™ in vivo imaging system (Cambridge Research and Instrumentations Inc.). Both data sets were acquired using the Maestro™ "flat-field" correction functionality to compensate for possible illumination field inhomogeneities. The data sets were also single-binned to maximize resolution. Exposure times were selected via the Maestro™ "AutoExpose" data collection option. The first image data set was excited in the NIR range (FIG. 3A) and collected the emission photon at 780-950 nm. The second image data set was excited in the visible range (500-620 nm) and, the emission photon was collected in the 550-800 nm range. Emission data was collected in 10 nm increments over the corresponding emission ranges. The two image data sets were saved as tow collections of 1392× 1040.TIF files.

The TIF: File data sets were imported into Matlab for analysis. To assemble the contributions from each wavelength's .TIF file to the total image signal intensity over the entire emission range, each data set was integrated over all emission wavelengths on a pixel by pixel basis. A built-in Matlab trapezoidal integration function was used to calculate the integral of all 1392×1040 pixels' intensities over the emission range to yield an associated 1392×1040 matrix of values corresponding to the area under the curve of each pixels' spectra.

Subsequent to the generation of each data set's integral matrix, pixels in the Maestro field of view (FOV) in which no dye signal was displayed were isolated as background (BG), identified by manual drawing of a region of interest outside of the dye samples. The mean and standard deviation of the BG signal were then calculated. A normal distribution was assumed for the BG. Thus, it was considered that greater than 99% of the BG signals fall within the range of the mean BG ± three standard deviations of BG. Based on this assumption, a threshold value for determination of significant signal was established as BG + three standard deviations of BG. All pixels displaying intensity signals less than this threshold were assigned a value of zero. All pixels displaying intensity values greater than this threshold were considered significant. Significant intensity values were assigned one of the dye samples via manual drawing of regions of interest. Contributions from BG outside of the portion of the FOV covered by the dye samples were thus separated from the total signal intensity from each dye sample in each data set. The total signal intensity from each dye sample was then calculated as the sum of all non-zero values in the corresponding ROI and expressed as a fraction of the total image signal intensity.

From this calculation, we found that if the NIR820 and 4-SULFONIR were used to image two events in one environment, excitation in the NIR window (>750 nm) will cause the former to emit strong fluorescent signal and the later to emit about 10% of the signal compared to the former one. Meanwhile, if we want to monitor the event linked to 4-SULFONIR, the process could be carried out by excitation in the visible range. In this domain, the 4-SULFONIR emits very strong signal while the other has about 20% of the signal compared to 4-SULFONIR.

Example 6

Labeling of a Biological Molecule with an Amine Reactive Group

This example demonstrates labeling a biological molecule with an amine reactive group. This procedure can be achieved as the procedure described for thiol-reactive groups, below, except the pH level should be adjusted to pH=8.5.

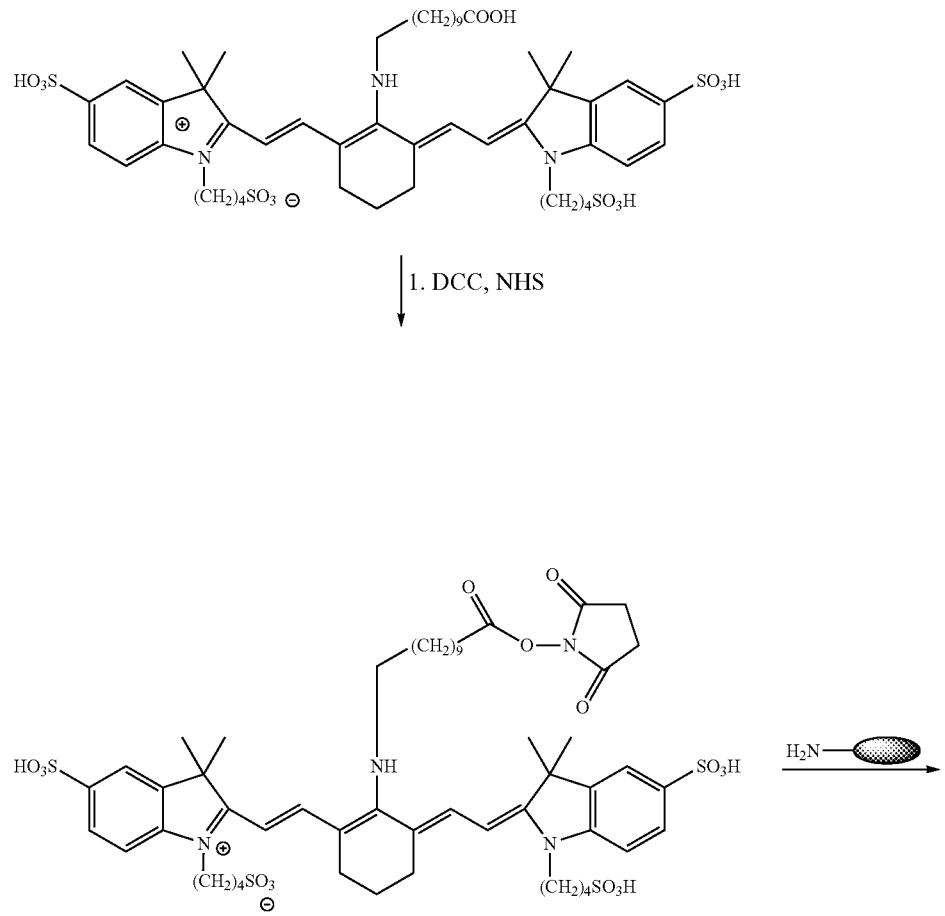

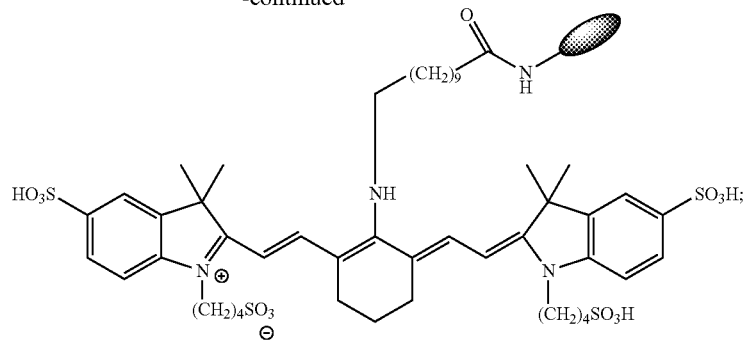

wherein ⬬ is a peptide, protein, or antibody. Examples include Lysine or the N-terminal of any amino acid.

Example 7
Labeling of a Biological Molecule with a Thiol Reactive Group

This example demonstrates labeling a biological molecule with a thiol reactive group. 4-Sulfonir maleimide (1.0 mg) is incubated with one equivalent of thiol-reactive materials that include peptides, proteins, antibodies and small organic molecules in 400 μL of buffer (1:1 acetonitrile/50 mM sodium acetate, pH=7.4) at room temperature in the dark with random shaking for 2 h. The labeled product is either purified by going through a size cut-off Centricon® filter or by HPLC.

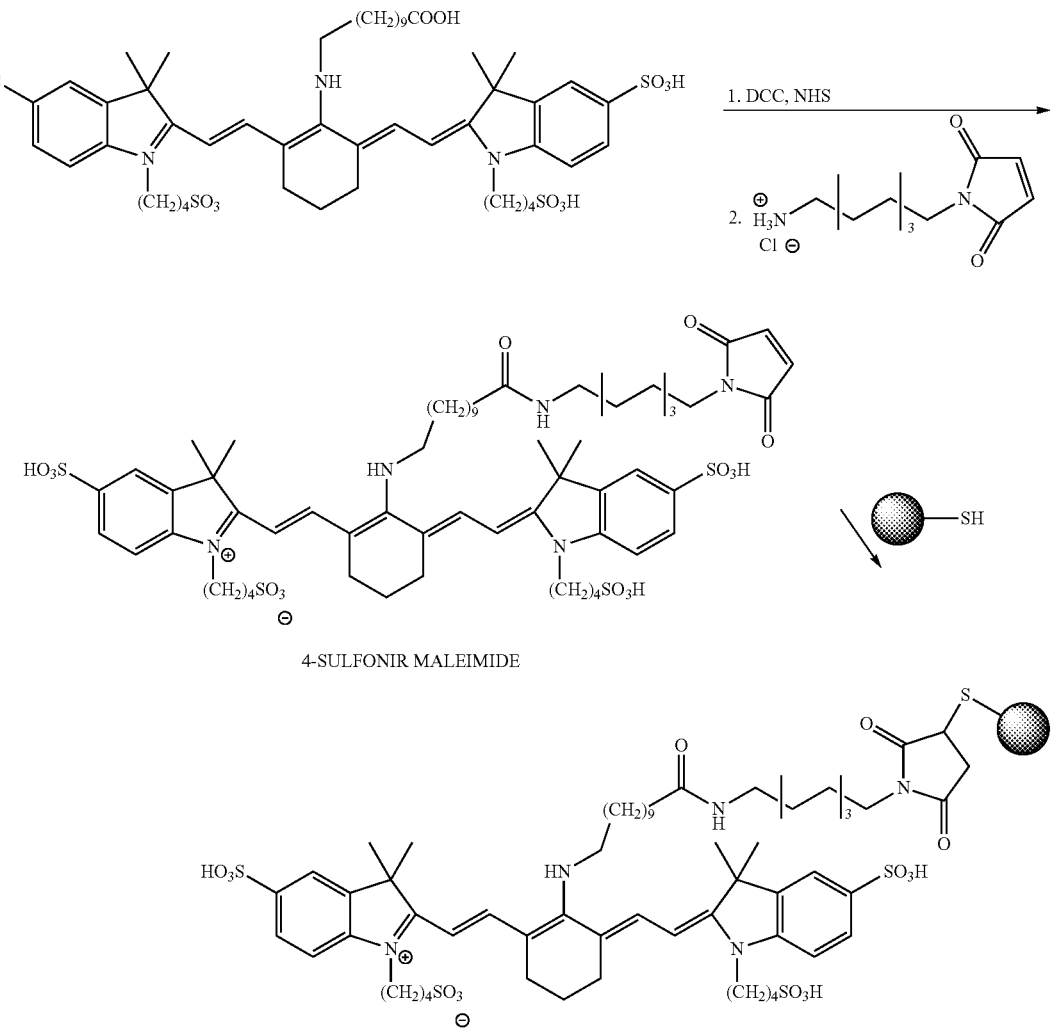

4-SULFONIR MALEIMIDE wherein ⬤
is a peptide, protein, or antibody. An example includes cystine.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications are referenced. All such references, specifically including those listed below, are incorporated herein by reference.

References

Achilefu, S.; Dorshow, R. B.; Bugaj, J. E.; Rajagopalan, R. Invest Radiol 2000, 35, (8), 479-85.

Becker, A.; Hessenius, C.; Bhargava, S.; Grotzinger, C.; Licha, K.; Schneider-Mergener, J.; Wiedenmann, B.; Semmler, W. Ann N Y Acad Sci 2000, 921, 275-8.

Bremer, C.; Tung, C. H.; Weissleder, R. Nat Med 2001, 7, (6), 743-8.

Fabian, J.; Nakazumi, H.; Matsuoka, M. Chemical Reviews (Washington, D.C., United States) 1992, 92, (6), 1197-1226.

Licha, K.; Hessenius, C.; Becker, A.; Henklein, P.; Bauer, M.; Wisniewski, S.; Wiedenmann, B.; Semmler, W. Bioconjug Chem 2001, 12, (1), 44-50.

Marten, K.; Bremer, C.; Khazaie, K.; Sameni, M.; Sloane, B.; Tung, C. H.; Weissleder, R. Gastroenterology 2002, 122, (2), 406-14.

Medarova, Z.; Pham, W.; Farrar, C.; Petkova, V.; Moore, A. Nat Med 2007, 13, (3), 372-377.

Medarova, Z.; Pham, W.; Kim, Y.; Dai, G.; Moore, A. Int J Cancer 2006, 118, (11), 2796-802.

Peng, X.; Song, F.; Lu, E.; Wang, Y.; Zhou, W.; Fan, J.; Gao, Y. J Am Chem Soc 2005, 127, (12), 4170-1.

Pham, W.; Choi, Y.; Weissleder, R.; Tung, C. H. Bioconjug Chem 2004, 15, (6), 1403-7.

Pham, W.; Medarova, Z.; Moore, A. Bioconjug Chem 2005, 16, (3), 735-40.

Pham, W.; Zhao, B. Q.; Lo, E. H.; Medarova, Z.; Rosen, B.; Moore, A. Neuroimage 2005, 28, (1), 287-92.

Tung, C.-H.; Bredow, S.; Mahmood, U.; Weissleder, R. Bioconjugate Chem 1999, 10, (5), 892-896.

Tung, C. H.; Mahmood, U.; Bredow, S.; Weissleder, R. Cancer Res 2000, 60, (17), 4953-8.

Weissleder, R.; Tung, C. H.; Mahmood, U.; Bogdanov, A., Jr. Nat. Biotechnol 1999, 17, (4), 375-8.

Zaheer, A.; Lenkinski, R. E.; Mahmood, A.; Jones, A. G.; Cantley, L. C.; Frangioni, J. V. Nat Biotechnol 2001, 19, (12), 1148-54.

The invention claimed is:

1. A compound of the following formula:

[Structure of cyanine dye with $R_1$, $R_2$, $R_3$ substituents and $(CH_2)_4SO_3^-$ / $(CH_2)_4SO_3H$ groups on indole nitrogens]

wherein $R_1$ is $SO_3H$; $R_2$ is chosen from carboxylic acid group and $SO_3H$; and $R_3$ is chosen from:

[Structure: $-NH-CH_2-CH_2-(CH_2)_8COOH$]

[Structure: $-NH-CH_2-CH_2-(CH_2)_{1-10}-C(=O)-O-N$-succinimidyl]

[Structure: $-NH-CH_2-CH_2-(CH_2)_8-C(=O)-O-N$-succinimidyl]

an amino-succinimidyl ester group, or an amino-maleimide group

2. The compound of claim 1, wherein $R_1$ and $R_2$ are $SO_3H$.

3. The compound of claim 1, wherein $R_3$ is:

[Structure: $-NH-CH_2-CH_2-(CH_2)_8COOH$]

4. The compound of claim 1, wherein $R_3$ is:
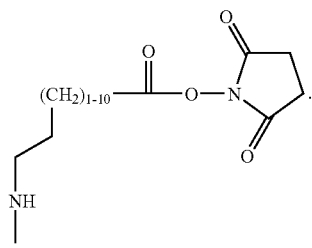
5. The compound of claim 1, wherein $R_3$ is
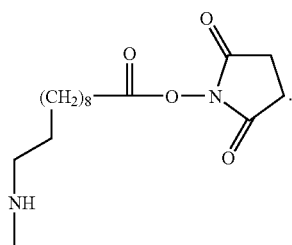
6. The compound of claim 1, wherein $R_3$ is chosen from an amino-succinimidyl ester group and an amino-maleimide group.
7. A compound of claim 1 of the following formula:
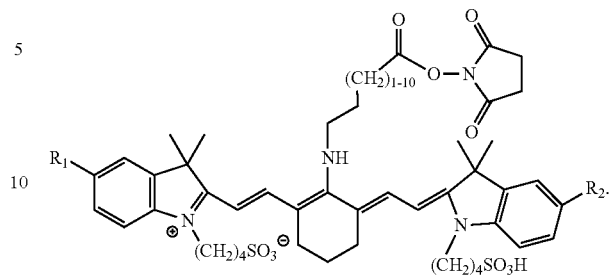
8. A compound of claim 1 of the following formula:
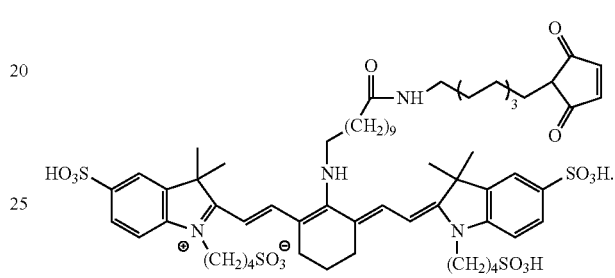
* * * * *